United States Patent
Matsumoto et al.

(10) Patent No.: US 7,691,191 B2
(45) Date of Patent: Apr. 6, 2010

(54) ANTHRAPYRIDONE COMPOUND, SALT THEREOF, MAGENTA INK COMPOSITION AND COLORED PRODUCT

(75) Inventors: Hiroyuki Matsumoto, Kita-ku (JP); Noriko Kajiura, Kita-ku (JP); Yutaka Ishii, Kita-ku (JP); Yasuo Murakami, Kita-ku (JP)

(73) Assignee: Nippon Kayaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 12/312,791

(22) PCT Filed: Nov. 27, 2007

(86) PCT No.: PCT/JP2007/072821

§ 371 (c)(1),
(2), (4) Date: May 26, 2009

(87) PCT Pub. No.: WO2008/066024

PCT Pub. Date: Jun. 5, 2008

(65) Prior Publication Data

US 2010/0015410 A1    Jan. 21, 2010

(30) Foreign Application Priority Data

Nov. 29, 2006    (JP)    ............... 2006-322659

(51) Int. Cl.
C09D 11/02    (2006.01)
C09B 5/14    (2006.01)
B32B 3/10    (2006.01)
B41J 2/01    (2006.01)

(52) U.S. Cl. .............. 106/31.47; 546/76; 428/195.1; 347/100

(58) Field of Classification Search .......... 106/31.47; 546/76; 428/195.1; 347/100
See application file for complete search history.

(56) References Cited

U.S. PATENT DOCUMENTS

| | | | |
|---|---|---|---|
| 4,902,798 A | 2/1990 | Nakamatsu et al. | 546/76 |
| 5,367,075 A | 11/1994 | Nakamatsu et al. | 546/76 |
| 6,152,969 A | 11/2000 | Matsumoto et al. | 8/658 |
| 6,471,760 B1 * | 10/2002 | Matsumoto et al. | 106/31.47 |
| 6,843,839 B2 * | 1/2005 | Kanke et al. | 106/31.47 |
| 6,852,154 B2 * | 2/2005 | Kitamura et al. | 106/31.47 |
| 6,929,361 B2 * | 8/2005 | Matsumoto et al. | 106/31.47 |
| 6,984,032 B2 * | 1/2006 | Kitamura et al. | 106/31.47 |
| 7,015,327 B2 * | 3/2006 | Matsumoto et al. | 546/76 |
| 7,223,301 B2 * | 5/2007 | Matsumoto et al. | 106/31.47 |
| 7,416,592 B2 * | 8/2008 | Kitamura et al. | 106/31.47 |
| 7,618,484 B2 * | 11/2009 | Fujimoto et al. | 106/31.47 |
| 2004/0239739 A1 | 12/2004 | Matsumoto et al. | 347/100 |
| 2005/0171351 A1 | 8/2005 | Matsumoto et al. | 546/76 |
| 2009/0047430 A1 * | 2/2009 | Mori et al. | 347/100 |

FOREIGN PATENT DOCUMENTS

| | | |
|---|---|---|
| JP | 63-139170 | 6/1988 |
| JP | 11-29714 | 2/1999 |
| JP | 2000-256587 | 9/2000 |
| JP | 2001-354881 | 12/2001 |
| JP | 2003-335989 | 11/2003 |
| JP | 2005-307067 | 11/2005 |
| JP | 2005-307068 | 11/2005 |
| JP | 2006-083330 | 3/2006 |
| JP | 2007-77256 | 3/2007 |
| WO | 98/11167 | 3/1998 |
| WO | 03/027185 | 4/2003 |

OTHER PUBLICATIONS

International Search Report dated Jan. 8, 2008 (PCT/JP2007/072909 in co-pending U.S. Appl. No. 12/312,779).
International Search Report dated Jan. 29, 2008 (PCT/JP2007/071631 in co-pending U.S. Appl. No. 12/312,274).

* cited by examiner

Primary Examiner—Helene Klemanski
(74) Attorney, Agent, or Firm—Nields, Lemack & Frame, LLC

(57) ABSTRACT

The present invention relates to a novel anthrapyridone compound represented by the following formula (1) or a salt thereof, and can provide a magenta coloring matter having a highly vivid hue suitable for inkjet recording, a high fastness to recorded matters, and an excellent storage stability;

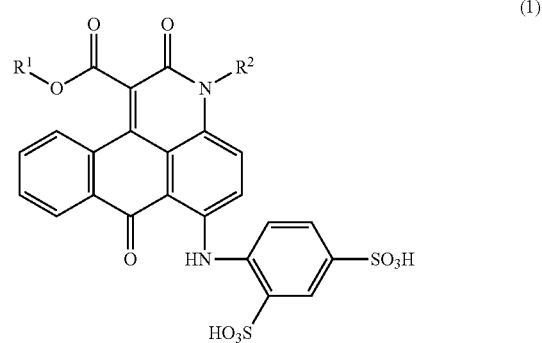

(1)

wherein $R^1$ represents a benzyl group wherein the phenyl group of the benzyl group may be further substituted by a methyl group, a chlorine atom or a nitro group, 1-naphthylmethyl group or the like, and $R^2$ represents a hydrogen atom, an alkyl group or the like, respectively.

18 Claims, No Drawings

ANTHRAPYRIDONE COMPOUND, SALT THEREOF, MAGENTA INK COMPOSITION AND COLORED PRODUCT

TECHNICAL FIELD

The present invention relates to a novel anthrapyridone compound, a magenta ink composition containing the anthrapyridone compound and a colored product colored with this composition and the like.

BACKGROUND ART

In the recording method by means of an inkjet printer which is one of the typical methods among various color recording methods, various methods for discharging ink have been developed. In any of the methods, ink droplets are generated and adhered onto various record-receiving materials (such as paper, film and cloth) to perform recording. This has been rapidly prevailing lately and is expected to continue growing remarkably in the future because of features such as quietness without noise generation due to no direct contact of a recording head with a record-receiving material and as easiness in downsizing, speedup and colorization.

Conventionally, as an ink for fountain pens, felt-tip pens or the like and as an ink for inkjet recording, water-based inks where a water-soluble dye is dissolved in an aqueous medium have been used. In these water-based inks, a water-soluble organic solvent is generally added to prevent ink from clogging at a pen tip or an inkjet nozzle. These conventional inks are required to provide recorded images with sufficient density, not to clog at a pen tip or a nozzle, to dry quickly on a record-receiving material, to bleed less, to have an excellent storage stability, and so on. In addition, formed images are required to have fastnesses such as water fastness, light fastness and moisture fastness.

Meanwhile, images or character information on color displays of computers are generally expressed by subtractive color mixing of 4 primary color inks of yellow (Y), magenta (M), cyan (C) and black (K) for color recording by an ink jet printer. In order that the hues of an image expressed by additive color mixing of red (R), green (G) and blue (B) on CRT displays and the like is, as faithfully as possible, reproduced with images expressed by subtractive color mixing, it is desired that each of Y, M and C has a hue as close to each standard as possible and also is vivid. In addition, it is required that ink compositions to be used for them are stable in storage for a long period of time, and that images printed therewith have a high concentration and said images are excellent in fastnesses such as water fastness, light fastness, and gas fastness.

The application of inkjet printers has been widely spread in the fields ranging from small printers for office automation to large printers for industrial use, and therefore fastnesses such as water fastness, moisture fastness, light fastness and gas fastness have been required more than ever.

Water fastness has been largely improved by coating organic or inorganic particulates of porous silica, cation polymer, aluminasol, special ceramic and the like together with a PVA resin on a paper surface to provide an image receiving layer on a record-receiving material, and otherwise. "Moisture fastness" means durability against a phenomenon that the dye in a record-receiving material bleeds around the colored image when the colored record-receiving material is stored under an atmosphere of high humidity. Dye bleeding extremely deteriorates image quality in images particularly required to have a high resolution and photo-like image quality, and therefore it is important to reduce such bleeding as far as possible. As for light fastness, technique for large improvement thereof has not established yet. In particular, many of coloring matters for magenta among 4 primary colors of Y, M, C and K originally have low light fastness, and therefore improvement thereof is an important problem.

In addition, there are more opportunities to print pictures at home with recent spread of digital cameras, and image discoloration by oxidizing gases such as ozone gas and nitrogen oxides in the air where printed matters obtained are stored is acknowledged as a problem. Oxidizing gas has a nature to react with dyes on or in a recorded paper, causing discoloration or fading of the printed image. Among oxidizing gasses, ozone gas is regarded as a main causative matter accelerating color-fading phenomenon of inkjet-recorded images. This phenomenon of discoloration or fading is characteristic of inkjet images, and therefore improvement of ozone gas fastness is also an important problem.

As a magenta coloring matter used in water-soluble inks for inkjet recording, typical are xanthene based coloring matters and azo based coloring matters using H acid (1-amino-8-hydroxy-naphthalene-3,6-disulfonic acid). However, it is known that the former is very excellent in hue and vividness but very inferior in light fastness. On the other hand, in the latter, some are good in terms of hue and water fastness, but many are inferior in light fastness and vividness. In addition, as for this type, a magenta dye relatively excellent in vividness and light fastness has been developed but it still has a low level in light fastness compared with dyes having a different hue such as a cyan dye represented by a copper phthalocyanine-based coloring matter and a yellow dye.

Examples of a coloring matter for magenta excellent in vividness and light fastness include an anthrapyridone-based coloring matter (see, for example, Patent Literatures 1 to 11), but a coloring matter for magenta satisfying all the requirements of hue, vividness, light fastness, water fastness, moisture fastness, gas fastness and dissolving stability has yet to be obtained.

In particular, Patent Literature 1 discloses a compound represented by the formula (1) described later where $R^1$ is an alkyl group such as, for example, methyl, ethyl and butyl, however these compounds do not satisfy all the requirements of hue, vividness, light fastness, water fastness, moisture fastness, gas fastness and dissolving stability.

[Patent Literature 1] JP H10-306221 A (pp. 1 to 3 and 7 to 18)

[Patent Literature 2] JP 2000-109464 A (pp. 1 to 2 and 8 to 12)

[Patent Literature 3] JP 2000-169776 A (pp. 1 to 2 and 6 to 9)

[Patent Literature 4] JP 2000-191660 A (pp. 1 to 3 and 11 to 14)

[Patent Literature 5] JP 2000-256587 A (pp. 1 to 3 and 7 to 18)

[Patent Literature 6] JP 2001-72884 A (pp. 1 to 2 and 8 to 11)

[Patent Literature 7] JP 2001-139836 A (pp. 1 to 2 and 7 to 12)

[Patent Literature 8] WO 2004/104108 A1 (pp. 20 to 36)

[Patent Literature 9] JP 2003-192930 A (pp. 1 to 4 and 15 to 18)

[Patent Literature 10] JP 2005-8868 A (pp. 1 to 3 and 15 to 22)

[Patent Literature 11] JP 2005-314514 A (pp. 1 to 3 and 15 to 20)

DISCLOSURE OF THE INVENTION

Problems to be Solved by the Invention

It is an object for the present invention to provide a magenta coloring matter (compound) which is high in solubility in water, has a hue and vividness suitable for inkjet recording and enables a recorded matter excellent in various fastnesses, particularly moisture fastness, and an ink composition containing it.

Means of Solving the Problems

The present inventors have intensively studied to solve the above problems and found that an anthrapyridone compound represented by the following formula (1) can solve the above problems, and have now completed the present invention. That is, the present invention relates to:

(1) An anthrapyridone compound represented by the following formula (1) or a salt thereof, Formula (1)

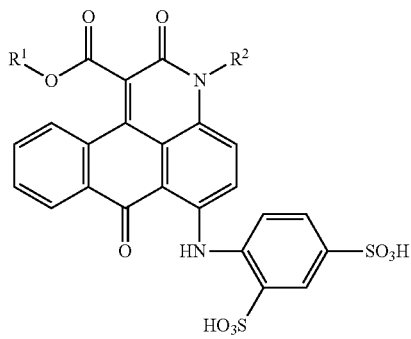

(wherein $R^1$ represents a benzyl group (where the phenyl group in the benzyl group may be substituted by a group selected from the group consisting of a methyl group, a chlorine atom and a nitro group), a 1-naphthylmethyl group, a phenacyl group or a cyanopropyl group, and $R^2$ represents a hydrogen atom, an alkyl group, a lower alkoxy lower alkyl group, a hydroxy lower alkyl group, a cyclohexyl group, a (mono- or di-alkylamino) alkyl group or a cyano lower alkyl group, respectively), (2) The anthrapyridone compound or a salt thereof according to the above (1), wherein $R^1$ is a benzyl group (where the phenyl group in the benzyl group may be substituted by a group selected from the group consisting of a methyl group, a chlorine atom and a nitro group), a 1-naphthylmethyl group, a phenacyl group or a 3-cyanopropyl group, and $R^2$ is a hydrogen atom, a C1 to C4 alkyl group, a C1 to C4 alkoxy C1 to C4 alkyl group, a hydroxy C1 to C4 alkyl group, a cyclohexyl group, a (mono or di-C1 to C4 alkylamino) C1 to C4 alkyl group or a cyano C1 to C4 alkyl group, (3) The anthrapyridone compound or a salt thereof according to the above (1) or (2), wherein $R^1$ is a benzyl group (where the phenyl group in the benzyl group may be substituted by a group selected from the group consisting of a methyl group, a chlorine atom and a nitro group), a 1-naphthylmethyl group, a phenacyl group or a 3-cyanopropyl group, and $R^2$ is a hydrogen atom, a C1 to C4 alkyl group, a 3-methoxypropyl group, a 2-hydroxyethyl group, a 3-dimethylaminopropyl group or a 2-cyano ethyl group, (4) The anthrapyridone compound or a salt thereof according to the above (1), wherein $R^1$ is a benzyl group (where the phenyl group in the benzyl group may be substituted by a group selected from the group consisting of a methyl group, a chlorine atom and a nitro group), and $R^2$ is a C1 to C4 alkyl group, (5) The anthrapyridone compound or a salt thereof according to the above (1), wherein $R^1$ is benzyl, methylbenzyl or 1-naphthylmethyl, and $R^2$ is methyl, (6) The anthrapyridone compound or a salt thereof according to the above (1) or (4), which is represented by the following formula (2), Formula (2)

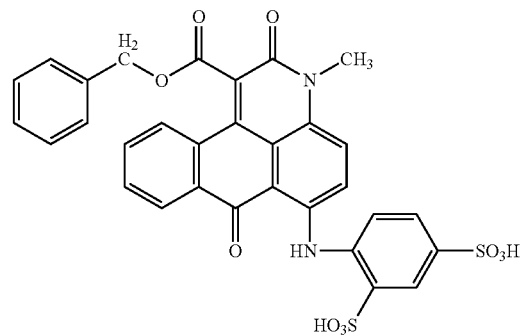

(7) The anthrapyridone compound or a salt thereof according to the above (1) or (4), which is represented by the following formula (9), Formula (9)

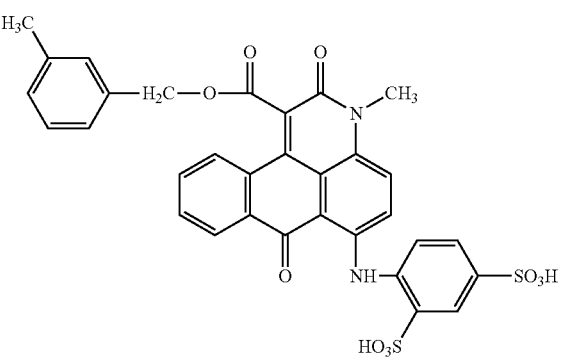

(8) An ink composition characterized by containing the anthrapyridone compound or a salt thereof according to any one of the above (1) to (7), (9) The ink composition according to the above (8), which contains water and a water-soluble organic solvent,

(10) The ink composition according to the above (9), which is for inkjet recording,

(11) The ink composition according to the above (8) to (10), wherein the content of an inorganic salt contained in the total amount of the anthrapyridone compound or a salt thereof according to any one of the above (1) to (7) is 1% by weight or below,

(12) The ink composition according to any one of the above (8) to (11), wherein the content of the anthrapyridone compound or a salt thereof according to any one of the above (1) to (7) is 0.1 to 20% by weight,

(13) An inkjet recording method characterized by discharging droplets of the ink composition according to any one of the above (8) to (12) in response to a recording signal to record on a record-receiving material,

(14) The inkjet recording method according to the above (13), wherein the record-receiving material is a communication sheet,

(15) The inkjet recording method according to the above (14), wherein the communication sheet has an ink receiving layer containing a porous white inorganic substance,

(16) A colored product colored with the ink composition according to any one of the above (8) to (12),

(17) The colored product according to the above (16), wherein coloring is carried out by an inkjet printer,

(18) An inkjet printer in which a container containing the ink composition according to any one of the above (8) to (12) is installed.

EFFECT OF THE INVENTION

The anthrapyridone compound of the above formula (1) of the present invention has characteristics to exhibit a very vivid hue on inkjet recording paper, be excellent in water-solubility, and have good filtration properties to a membrane filter in the production process of an ink composition. In addition, the ink composition of the present invention using this compound is free from crystal precipitation, changes in physical properties and color, and the like after storage for a long period of time, and thus it has a good storage stability. Further, a printed matter using the anthrapyridone compound of the present invention as a magenta ink for inkjet recording has an ideal magenta hue without selecting a record-receiving material (paper, film and the like). Furthermore, the magenta ink composition of the present invention also enables the hue of a photo-like color image to be faithfully reproduced on paper. Moreover, even when recording is carried out on a record-receiving material coated with inorganic particles on the surface thereof, such as inkjet special paper or film for photo image quality, the anthrapyridone compound of the present invention provides the recorded image with various good fastnesses such as light fastness, ozone gas fastness and the like, particularly moisture fastness, and thus provides the photo-like recorded image with an excellent long-term storage stability. Therefore, the anthrapyridone compound of the above formula (1) is extremely useful as a magenta coloring matter for inkjet recording.

BEST MODE FOR CARRYING OUT THE INVENTION

The present invention will be specifically explained. The anthrapyridone compound or a salt thereof of the present invention is represented by the above formula (1).

In the present description, the term "alkyl" typically used means alkyl having about 1 to 15 carbon atoms and is preferably alkyl having 1 to 8 carbon atoms, and examples thereof include, for example, methyl, ethyl, n-propyl, iso-propyl, n-butyl, sec-butyl, t-butyl, iso-butyl, n-pentyl, n-hexyl, n-heptyl or n-octyl. Further, in the term "alkoxy" and the like, with respect to the alkyl group moiety of groups thereof, the alkyl means that it has the same number of carbon atoms as the above alkyl.

In addition, when describing "lower alkyl", examples of said lower alkyl can typically include alkyl having 1 to 6 carbon atoms and preferably 1 to 4 carbon atoms among the above alkyl. Preferable specific examples thereof can include methyl, ethyl, n-propyl, iso-propyl, n-butyl, iso-butyl, sec-butyl and t-butyl.

In the present description, when describing "lower", for convenience, in a group except for lower alkyl, for example lower alkoxy and the like, it also means to have carbon atoms in the same range as above, unless otherwise specified.

In the description of substituent and the like in the present description, the group is typically meant to be unsubstituted unless specified that it may have a substituent.

In addition, the superscript "®" in the present description denotes a registered trademark.

In the formula (1), $R^1$ represents a substituted or unsubstituted benzyl group, a 1-naphthylmethyl group, a phenacyl group or a cyanopropyl group. In this regard, examples of the substituted benzyl group for $R^1$ can include a benzyl group where the phenyl group is substituted by a group selected from the group consisting of a methyl group, a chlorine atom and a nitro group.

When $R^1$ is a cyanopropyl group, the substitution position of the cyano may be any of the 1-, 2- and 3-positions to the propyl, and preferable is the 3-position.

Examples of the substituent on the phenyl group of the above substituted benzyl group for $R^1$ include a group selected from the group consisting of, as described above, a methyl group, a chlorine atom and a nitro group, preferable is methyl or a chlorine atom, and more preferable is methyl. The position of these substituents may be any position on the phenyl group where substitution can be performed, and typically the 3-position or the 4-position on the benzyl group is preferred and the 3-position is more preferred. The substituted or unsubstituted benzyl group for $R^1$ is preferably benzyl or methylbenzyl and more preferably 3-methylbenzyl.

$R^1$ is preferably a benzyl group which is unsubstituted or the above group-substituted, or 1-naphthylmethyl, more preferably the former, further preferably benzyl or methylbenzyl and most preferably 3-methylbenzyl.

In the above formula (1), $R^2$ represents a hydrogen atom, an alkyl group, a lower alkoxy lower alkyl group, a hydroxy lower alkyl group, a cyclohexyl group, a (mono- or di-alkylamino) alkyl group or a cyano lower alkyl group, respectively.

Examples of the alkyl group for $R^2$ include the above alkyl, and the carbon number is preferably in the range of typically 1 to 8, preferably 1 to 6 and further preferably 1 to 4. Specific examples thereof include the groups described in the above explanation of the term "alkyl", preferable are the groups described in explanation of the term "lower alkyl" and most preferable is methyl.

The lower alkoxy lower alkyl group for $R^2$ is preferably a C1 to C4 alkoxy C1 to C4 alkyl group. Specific examples thereof include, for example, methoxymethyl, ethoxymethyl, propoxymethyl, butoxymethyl, methoxyethyl, ethoxyethyl, propoxyethyl, butoxyethyl, methoxypropyl, ethoxypropyl, propoxypropyl, butoxypropyl, methoxybutyl, ethoxybutyl, propoxybutyl and butoxybutyl, and preferable is methoxypropyl. The alkoxy and the alkyl in the lower alkoxy lower alkyl group may be linear, branched, or cyclic, and the both are preferably linear. When $R^2$ is a lower alkoxy lower alkyl group, it is most preferably 3-methoxypropyl.

The hydroxy lower alkyl group for $R^2$ is preferably a hydroxy C1 to C4 alkyl group. Specific examples thereof include, for example, hydroxymethyl, hydroxyethyl, hydroxypropyl and hydroxybutyl. The alkyl in the hydroxy lower alkyl group may be linear, branched or cyclic, and is particularly preferably linear. The substitution position of the hydroxy in said lower alkyl may be any position, however the substitution is preferably performed at the terminal position. Specifically, such a hydroxy lower alkyl group is, for example, 2-hydroxyethyl, 3-hydroxypropyl or 4-hydroxybutyl. The hydroxy lower alkyl group for $R^2$ is more preferably 2-hydroxyethyl.

The (mono- or di-alkylamino) alkyl group for $R^2$ is preferably a (mono- or di-C1 to C4 alkylamino) C1 to C4 alkyl group. Specific examples thereof include, for example, (monomethylamino)propyl, (monoethylamino)propyl, (dimethylamino)propyl, (diethylamino)ethyl and the like, and preferable is 3-dimethylaminopropyl.

The cyano lower alkyl group for $R^2$ is preferably a cyano C1 to C4 alkyl group. Specific examples thereof include, for example, cyanomethyl, cyanoethyl, cyanopropyl and cyanobutyl. The alkyl in the cyano lower alkyl group may be linear, branched or cyclic, and is particularly preferably linear. The substitution position of the cyano in said alkyl may be any position, however the substitution is preferably performed at the terminal position. Specifically, such a cyano lower alkyl group is, for example, 2-cyanoethyl, 3-cyanopropyl or 4-cyanobutyl. When $R^2$ is a cyano lower alkyl group, 2-cyanoethyl is particularly preferred.

$R^2$ is preferably a hydrogen atom, an alkyl group, a cyclohexyl group, or a cyano lower alkyl group and more preferably a hydrogen atom or an alkyl group (preferably a C1 to C4 alkyl group).

In addition, optionally, a hydrogen atom, a C1 to C4 alkyl group, a C1 to C4 alkoxy C1 to C4 alkyl group, a hydroxy C1 to C4 alkyl group, a cyclohexyl group, a (mono- or di-C1 to C4 alkylamino) C1 to C4 alkyl group or a cyano C1 to C4 alkyl group is preferred, and more preferred is a hydrogen atom, a C1 to C4 alkyl group, a 3-methoxypropyl group, a 2-hydroxyethyl group, a 3-dimethylaminopropyl group or a 2-cyano ethyl group. A C1 to C4 alkyl group is further preferred, and methyl is most preferred.

The combination of $R^1$ and $R^2$ in the compound of the above formula (1) is preferably a combination of preferable groups described above for $R^1$ and $R^2$ and more preferably a combination where a more preferable group described above is used for any one of $R^1$ and $R^2$. A combination of more preferable groups or of a more preferable group and a further preferable group for $R^1$ and $R^2$ is further preferred, and a combination of further preferable groups or of a further preferable group and the most preferable group for $R^1$ and $R^2$ is most preferred.

More specifically, preferable is a combination of $R^1$ and $R^2$ which are described in (2) to (3) in the section "Means of Solving the Problems" described above. More preferable is a combination where $R^1$ is an unsubstituted benzyl group or a substituted benzyl group where the phenyl group is substituted by a group selected from the group consisting of a methyl group, a chlorine atom and a nitro group (preferably methylphenylmethyl: which is referred to as methylbenzyl in the present description for simplicity) and $R^2$ is a C1 to C4 alkyl group. In addition, a combination where $R^1$ is 1-naphthylmethyl and $R^2$ is a C1 to C4 alkyl group is also preferred. In this connection, the C1 to C4 alkyl group for $R^2$ is preferably a methyl group.

One of the most preferable combinations is that $R^1$ is benzyl, methylbenzyl or 1-naphthylmethyl and $R^2$ is methyl. The salt of the compound of the above formula (1) is a salt with an inorganic or organic base. Said salt is preferably, for example, an alkali metal salt (for example, a lithium salt, a sodium salt, a potassium salt and the like) or a salt with a quaternary ammonium ion (quaternary ammonium salt) represented by the following formula (3).

Formula (3)

(3)

(wherein each of $Z^1$ to $Z^4$ independently represents a hydrogen atom, an alkyl group, a hydroxyalkyl group or a hydroxyalkoxyalkyl group.)

Examples of the alkyl group for $Z^1$ to $Z^4$ in the formula (3) include methyl and ethyl, examples of the hydroxyalkyl group include hydroxymethyl, 2-hydroxyethyl, 3-hydroxypropyl, 2-hydroxypropyl, 4-hydroxybutyl, 3-hydroxybutyl, 2-hydroxybutyl and the like, and examples of the hydroxyalkoxyalkyl group include hydroxyethoxymethyl, 2-hydroxyethoxyethyl, 3-hydroxyethoxypropyl, 3-hydroxyethoxybutyl, 2-hydroxyethoxybutyl and the like.

Among them, more preferable examples thereof include a sodium salt, a potassium salt, a lithium salt, a monoethanolamine salt, a diethanolamine salt, a triethanolamine salt, a monoisopropanolamine salt, a diisopropanolamine salt, a triisopropanolamine salt, an ammonium salt and the like. Among them, particularly preferable are a lithium salt, an ammonium salt and a sodium salt. In addition, in view of solubility in water, the salt of the compound represented by the above formula (1) is preferably an ammonium salt.

As for the production method of the above salt, for example, it is possible to obtain a sodium salt of the compound of the formula (1) as a wet cake by adding a sodium chloride to a reaction liquid containing the compound of the formula (1) or an aqueous solution dissolving a cake containing the compound of the formula (1) or a dried form thereof, salting out, and filtering. In addition, it is possible to obtain a compound represented by the formula (1) in free acid form by dissolving the obtained wet cake in water again, then adding hydrochloric acid thereto for adjusting the pH to 1 to 2, and separating obtained crystals by filtration. Further, it is also possible to obtain a mixture of the sodium salt and the free acid by controlling the addition amount of hydrochloric acid to appropriately adjust pH to a more neutral value and separating obtained crystals by filtration. The mixture ratio of the both can be appropriately controlled by adjusting the pH. Furthermore, while stirring the wet cake of free acid together with water, thereto, for example, a potassium hydroxide, a lithium hydroxide or ammonia water is added for adjusting to alkaline, and, thereby, it is possible to obtain a corresponding potassium, lithium or ammonium salt, respectively; or, a compound which becomes an organic ammonium ion represented by the above formula (3) in water is added thereto for adjusting to alkaline, and, thereby, it is possible to obtain an organic ammonium salt corresponding said organic ammonium ion. Moreover, it is also possible to obtain a mixed salt of sodium and potassium or a mixture of sodium, potassium and free acid by dissolving for example, a wet cake of a mixture of free acid and sodium salt in water and then adding a potassium hydroxide thereto. Among these salts, particularly preferable are a lithium salt, an ammonium salt and a sodium salt as described above.

Specific examples of the anthrapyridone compound represented by the above formula (1) of the present invention are shown in the following Table 1.

TABLE 1

| Compound No. | R 1 | R 2 |
|---|---|---|
| 1 | Benzyl | Methyl |
| 2 | 4-Methylbenzyl | Methyl |
| 3 | 3-Methylbenzyl | Methyl |
| 4 | 2-Methylbenzyl | Methyl |
| 5 | 4-Chlorobenzyl | Methyl |
| 6 | 4-Nitrobenzyl | Methyl |
| 7 | 1-Naphthyl methyl | Methyl |
| 8 | Benzyl | 3-Methoxypropyl |
| 9 | Benzyl | 2-Hydroxyethyl |
| 10 | Benzyl | 2-Cyanoethyl |
| 11 | Benzyl | 3-Dimethylaminopropyl |
| 12 | Phenacyl | Methyl |
| 13 | 3-Cyanopropyl | Methyl |
| 14 | Benzyl | H |
| 15 | 4-Methylbenzyl | H |

Hereinafter, the method for producing the compound of the present invention will be described. In this connection, $R^1$ and $R^2$ in the following formulas (101) to (105) have the same meanings as in the above formula (1).

The anthrapyridone compound of the present invention can be produced by using, as an intermediate, a compound of the following formula (103) obtained by, for example, the method described in Patent Literature 1 or a method similar to the method.

That is, to 1 mol of an anthraquinone compound represented by the following formula (101), 3 to 15 mol of aniline is added without a solvent or in an organic solvent such as isobutanol, and sodium acetate or potassium acetate is added in the presence of a catalyst such as copper acetate or copper (I) chloride. Subsequently, the reaction was carried out at a temperature of 80 to 150° C. for 1 to 10 hours. After that, the reaction liquid is cooled, and methanol is added thereto for precipitation of crystals to obtain a compound of the following formula (102).

Formula (101)

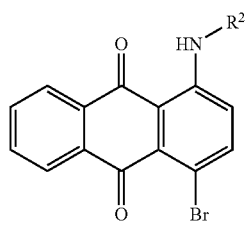

(101)

Formula (102)

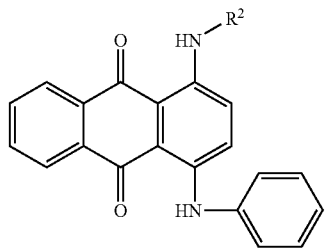

(102)

Subsequently, 1 mol of the obtained compound represented by the above formula (102) is reacted with 1 to 5 mol of diethylmalonate in a polar solvent such as xylene in the presence of a basic compound such as sodium carbonate at 130 to 180° C. for 5 to 15 hours so as to obtain a compound represented by the following formula (103).

Formula (103)

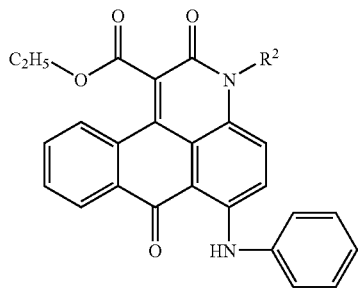

(103)

After 1 mol of the obtained compound of the above formula (103) is reacted in 5% to 20% fuming sulfuric acid at 50 to 100° C. for 15 minutes to 5 hours, the reaction liquid is added to ice water. Sodium chloride is added thereto to precipitate a solid, which is then separated by filtration and washed with an aqueous sodium chloride solution to obtain a compound of the following formula (104).

Formula (104)

(104)

Subsequently, after the obtained compound of the above formula (104) (which is a wet cake as it is, or its dried form) is dissolved in water, while adjusting the pH to 5 to 11 with alkali such as sodium hydroxide, a compound of the following formula (105) is added thereto at 50 to 100° C. and the reaction was carried out for 1 to 10 hours at the same temperature. After that, a salt such as sodium chloride is added thereto to precipitate a solid, and this precipitated solid is separated by filtration to obtain the compound of the present invention represented by the above formula (1).

Formula (105)

R¹-X   (105)

(wherein $R^1$ has the same meaning as described above, and X represents a chlorine atom, a bromine atom or an iodine atom.)

The compound of the above formula (1) can be obtained in free acid form or in its salt form. These compounds of the present invention are used as a free acid or a salt thereof, for example, an alkali metal salt, an alkali earth metal salt, an alkyl amine salt, an alkanolamines salt, an ammonium salt or the like. The production method by converting the various salts to the free acid and the production method by converting the free acid to the various salts or the various mixed salts or the mixture of the free acid and the salt are as described above.

When the compound represented by the above formula (1) is used, it is preferable to use the compound containing less inorganic impurities (inorganic salt) such as metal cation chloride and sulfate contained together with said compound. The content is about, for example, 1% by weight or below to the total amount of said compound, only as a guide. In order to produce a compound of the present invention with less inorganic impurities (inorganic salt), desalting treatment of the above obtained compound of the present invention may be carried out by, for example, a typical method with a reverse osmosis membrane.

The ink composition of the present invention is obtained in that the compound represented by the above formula (1) of the present invention or a salt thereof is dissolved in water or an aqueous solvent (water containing a water-soluble organic solvent which will be described later), according to necessity, together with an ink preparation agent and the like. For example, a reaction liquid containing the compound represented by the above formula (1) can also be directly used for production of the ink composition of the present invention. Alternatively, an intended product is separated from the above reaction liquid and dried by, for example, spray-drying so as to obtain a dried form, which can be then used for production of said ink composition. The ink composition of the present invention contains the compound of the present invention in an amount of typically 0.1 to 20% by weight, more preferably 1 to 15% by weight and further preferably 2 to 10% by weight. The ink composition of the present invention may contain 0 to 30% by weight of a water-soluble organic solvent and 0 to 10%, preferably 0 to 5% by weight, of an ink preparation agent, respectively. The rest is water.

Examples of the above water-soluble organic solvent include, for example, C1 to C4 alkanols such as methanol, ethanol, n-propanol, isopropanol, n-butanol, isobutanol, secondary butanol and tertiary butanol; carboxylic acid amides such as N,N-dimethylformamide or N,N-dimethylacetoamide; heterocyclic ureas such as 2-pyrrolidone, N-methyl-2-pyrrolidone, 1,3-dimethylimidazolidin-2-one and 1,3-dimethylhexahydropyrimid-2-one; ketones or keto alcohols such as acetone, methylethyl ketone and 2-methyl-2-hydroxypentan-4-one; cyclic ethers such as tetrahydrofuran and dioxane; mono-, oligo- or poly-alkylene glycols or thioglycols having a (C2 to C6) alkylene unite such as ethylene glycol, 1,2- or 1,3-propylene glycol, 1,2- or 1,4-butylene glycol, 1,6-hexylene glycol, diethylene glycol, triethylene glycol, tetraethylene glycol, dipropylene glycol, thiodiglycol, polyethylene glycol and polypropylene glycol; polyols (triol) such as glycerine and hexane-1,2,6-triol; polyhydric alcohol (C1 to C4) alkyl ethers such as ethylene glycol monomethyl ether, ethylene glycol monoethyl ether, diethylene glycol mono methyl ether, diethylene glycol monoethyl ether, diethylene glycol mono butyl ether, triethylene glycol monomethyl ether or triethylene glycol monoethyl ether; gamma-butyrolactones or dimethylsulfoxides.

Preferable among the above are isopropanol, glycerine, mono-, di- or tri-ethylene glycol, dipropylene glycol, 2-pyrrolidone, N-methyl-2-pyrrolidone and/or diethylene glycol mono butyl ether, and more preferable are isopropanol, glycerine, diethylene glycol mono butyl ether (butyl carbitol), 2-pyrrolidone and/or N-methyl-2-pyrrolidone. These water-soluble organic solvents are used alone or as a mixture thereof. Typically, it is preferable that about 2 to 5 kinds thereof are used appropriately in combination.

Hereinafter, the ink preparation agents which can be used in preparation of the ink composition of the present invention will be explained. Specific examples of the ink preparation agents include, for example, an antiseptic and fungicide, a pH adjuster, a chelating agent, a rust preventive agent, a water-soluble UV absorbing agent, a water-soluble polymer compound, a dye dissolving agent, a surfactant and the like.

Examples of the antiseptic and fungicide include, for example, compounds such as organic sulfur based compound, organic nitrogen sulfur based compound, organic halogen based compound, haloallylsulfone based compound, iodopropargyl based compound, N-haloalkylthio based compound, nitrile based compound, pyridine based compound, 8-oxyquinoline based compound, benzothiazole based compound, isothiazoline based compound, dithiol based compound, pyridineoxide based compound, nitropropane based compound, organic tin based compound, phenol based compound, quaternary ammonium salt based compound, triazine based compound, thiadiazine based compound, anilide based compound, adamantane based compound, dithiocarbamate based compound, brominated indanone based compound, benzyl bromoacetate based compound and inorganic salt based compound.

Example of the organic halogen based compound includes, for example, sodium pentachlorophenol.

Example of the pyridineoxide based compound includes, for example, sodium 2-pyridinethiol-1-oxide.

Examples of the isothiazoline based compound include, for example, 1,2-benzoisothiazolin-3-one, 2-n-octyl-4-isothiazolin-3-one, 5-chloro-2-methyl-4-isothiazolin-3-one, 5-chloro-2-methyl-4-isothiazolin-3-one magnesium chloride, 5-chloro-2-methyl-4-isothiazolin-3-one calcium chloride, 2-methyl-4-isothiazolin-3-one calcium chloride and the like.

In addition, examples of the antiseptic and fungicide include sodium sorbate, sodium benzoate and the like (for example, Proxel® GXL(S), Proxel® XL-2(S) which are trade names; all manufactured by Avecia Corp.; and the like), and further anhydrous sodium acetate and the like.

As the pH adjuster, any substance can be used as long as it can adjust the pH of the ink in the range of 7.5 to 11.0 without any adverse effect on the ink to be mixed. For example, examples thereof include alkanolamines such as diethanolamine and triethanolamine; alkali metal hydroxides such as lithium hydroxide, sodium hydroxide and potassium hydroxide; ammonium hydroxides (ammonia water); alkali metal carbonates such as lithium carbonate, sodium carbonate and potassium carbonate, or the like.

Examples of the chelating agent include, for example, sodium ethylenediaminetetraacetate, sodium nitrilotriacetate, sodium hydroxyethylethylenediaminetriacetate, sodium diethylenetriaminepentaacetate, sodium uracil diacetate and the like.

Examples of the rust preventive agent include, for example, hydrogen sulfite salts, sodium thiosulfate, ammonium thioglycolate, diisopropylammonium nitrite, pentaerythritol tetranitrate, dicyclohexylammonium nitrite and the like.

Examples of the water-soluble UV absorbing agent include, for example, sulfonated benzophenon, sulfonated benzotriazole and the like.

Examples of the water-soluble polymer compound include, for example, polyvinyl alcohol, cellulose derivatives, polyamines, polyimines and the like.

Examples of the dye dissolving agent include, for example, urea, ε-caprolactam, ethylene carbonate and the like.

Examples of the surfactant include, for example, an anionic surfactant, an amphoteric surfactant, a cationic surfactant, a nonionic surfactant and the like.

Examples of the anionic surfactant include alkylsulfocarboxylate, α-olefin sulfonate, polyoxyethylene alkyl ether acetate, N-acyl amino acid and a salt thereof, N-acylmethyltaurine salt, alkylsulfate polyoxyalkyl ether sulfate, alkylsulfate polyoxyethylene alkyl ether phosphate, rosin acid soap, castor oil sulfate, lauryl alcohol sulfate, alkylphenol type phosphate, alkyl type phosphate, alkylarylsulfonate, diethylsulfosuccinate, diethylhexylsulfosuccinate, dioctylsulfosuccinate and the like.

Examples of the cationic surfactant include 2-vinylpyridine derivatives, poly(4-vinylpyridine) derivatives and the like.

Examples of the amphoteric surfactant include lauryldimethylaminoacetic acid betaine, 2-alkyl-N-carboxymethyl-N-hydroxyethyl imidazolinium betaine, coconut oil fatty acid amide propyldimethylaminoacetic acid betaine, polyoctylpolyaminoethylglycine, imidazoline derivatives and the like.

Examples of the nonionic surfactant include ether types such as polyoxyethylene nonylphenyl ether, polyoxyethylene octylphenyl ether, polyoxyethylene dodecylphenyl ether, polyoxyethylene octylphenyl ether, polyoxyethylene oleyl ether, polyoxyethylene lauryl ether and polyoxyethylene alkyl ether; ester types such as polyoxyethylene oleic acid, polyoxyethylene oleate ester, polyoxy ethylene distearic acid ester, sorbitan laurate, sorbitan monostearate, sorbitan monooleate, sorbitan sesquioleate, polyoxyethylene monooleate and polyoxyethylene stearate; and acetylene alcohol types such as 2,4,7,9-tetramethyl-5-decyne-4,7-diol, 3,6-dimethyl-4-octyne-3,6-diol and 3,5-dimethyl-1-hexyn-3-ol (for example, Surfynol® 104E, 104PG 50, 82 and 465, and Olfine® STG, which are trade names; all manufactured by Nissin Chemical Industry Co., Ltd.; and the like). These ink preparation agents may be used alone or as a mixture thereof.

The ink composition of the present invention can be produced by dissolving the compound of the present invention of the formula (1) and/or a salt thereof (hereinafter also referred to as the present compound) in water or the above aqueous solvent (water containing a water-soluble organic solvent), according to necessity, together with the above ink preparation agents.

In the above production method, the sequence order of dissolving the components is not particularly limited. The present compound may be dissolved in water or the above aqueous solvent in advance and then ink preparation agents may be added thereto; or the present compound may be dissolved in water and then the aqueous solvent and ink preparation agents may be added thereto. In addition, the sequence order may be different from this; otherwise the aqueous solvent and ink preparation agents may be added to a reaction liquid of the present compound or a solution of the present compound undergone desalting treatment with a reverse osmosis membrane, so as to produce an ink composition. In preparation of said ink composition, as water to be used, water with less impurity such as ion-exchanged water or distilled water is preferred. In addition, according to necessity, microfiltration may be carried out using a membrane filter or the like to remove off foreign substances. Further, when said ink composition is used as an ink for inkjet printers, it is preferred that microfiltration is carried out. The pore size of a filter for microfiltration is typically 1 to 0.1 μm and preferably 0.8 to 0.2 μm.

The colored product of the present invention is a product colored with the above compound of the present invention. The material to be colored therewith is not limited, and examples thereof include, for example, paper, fiber and cloth (cellulose, nylon, wool and the like), leather, substrates for color filters and the like, but the material is not limited thereto. Examples of the coloring method include, for example, dip dyeing method, textile printing method and printing method such as screen printing, a method by inkjet recording and the like. In the present invention, a method by inkjet recording is preferred.

Examples of the record-receiving material (medium) which can be applied to the inkjet recording method of the present invention include, for example, communication sheets such as paper and film, fiber, leather and the like. The communication sheet is preferably surface-treated, specifically with an ink receiving layer on the substrate thereof. The ink receiving layer is provided by, for example, impregnation or coating of a cation polymer on the above substrate, or by coating the above substrate surface with a porous white inorganic substance which can absorb the coloring matter in the ink, such as porous silica, aluminasol and special ceramics, together with a hydrophilic polymer such as polyvinyl alcohol or polyvinyl pyrrolidone. Such a record-receiving material as provided with an ink receiving layer is called typically inkjet special paper (film) or glossy paper (film) and the like, and examples thereof include, for example, Pictorico® (which is manufactured by Asahi Glass Co., Ltd.), Professional Photopaper, Super Photopaper and Matte Photopaper (which are all manufactured by Canon Inc.), CRISPIA®, Photo Paper (glossy), Photo Matte Paper and Super Fine Glossy Film (which are all manufactured by Seiko Epson Corporation), Advanced Photo Paper, Premium Plus Photo Paper, Premium Glossy Film and Photo Paper (which are all manufactured by Hewlett Packard Japan, Ltd.), PhotoLike® QP (which is manufactured by KONICA Corporation) and the like. In addition, it is naturally possible to employ plain paper.

Above all, it is known that the images recorded on the record-receiving materials coated with a porous white inorganic substance on the surface thereof particularly has a more significant discoloration or fading by ozone gas. The water-based magenta ink composition of the present invention has an excellent fastness against gases including ozone gas, and therefore it has an effect especially in the case of recording on such a record-receiving material.

Examples of the porous white inorganic substance to be used for such an intended purpose include calcium carbonate, kaolin, talc, clay, diatom earth, synthesized amorphous silica, aluminum silicate, magnesium silicate, calcium silicate, aluminum hydroxide, alumina, lithopone, zeolite, barium sulfate, calcium sulfate, titanium dioxide, zinc sulfide, zinc carbonate and the like.

In order to record on a record-receiving material by the inkjet recording method of the present invention, for example, a container containing the ink composition of the present invention is placed in a predetermined position of an inkjet printer and recording may be carried out on a record-receiving material in a typical manner. In the inkjet recording method of the present invention, not only magenta of the present invention but also ink compositions of other colors such as yellow, cyan, green, orange and blue (or violet), and according to necessity, black can be used in combination. Each color ink composition is filled into each container, which is placed (installed) in a predetermined position of an inkjet printer in the same manner for the container containing the water-based magenta ink composition for inkjet recording of the present invention, and used. Examples of the inkjet printer include, for example, a piezo type inkjet printer utilizing mechanical vibration, a bubble Jet® type printer utilizing foam generated by heating, and the like.

The ink composition of the present invention exhibits a vivid magenta color, has a highly vivid hue particularly on inkjet glossy paper, and enables recorded images high in various fastnesses, particularly excellent in moisture fastness. In addition, it is highly safe to human beings.

The ink composition of the present invention is free from precipitation and separation during storage. In addition, when the ink composition of the present invention is used for inkjet recording, clogging does not occur at an injector (inkhead). The ink composition of the present invention has no change in physical properties even in intermittent use of a continuous ink jet printer.

EXAMPLES

Hereinafter, the present invention will be further specifically explained with reference to the examples. In the examples, "part(s)" and "%" are based on weight unless otherwise specified.

The compounds of the present invention obtained in the examples had a solubility of 100 g/L or more in water (at 25° C.).

Each compound in Examples is shown as a free acid, but was synthesized as a sodium salt unless otherwise specified. However, the present invention is not limited to a sodium salt, as described above.

In addition, the maximum absorption wavelength ($\lambda$max) of each compound in Examples is a measured value in an aqueous solution unless otherwise specified.

Synthesis Example 1

According to the example 1-1 of Patent Literature 1, 24.6 parts of 1-methylamino-4-anilinoanthraquinone, 0.75 parts of sodium carbonate, 30.0 parts of diethylmalonate and 75 parts of o-dichlorobenzene were placed in a reactor, heated to 170 to 175° C., and reacted for 10 hours. In the meantime, the reaction was carried out while removing ethanol and water produced as the reaction proceeded, out of the reaction system.

The reaction liquid was cooled, and 150 parts of methanol was added thereto and stirred for 1 hour to precipitate a solid, which was then separated by filtration. The resulting solid was washed with 100 parts of methanol followed by 300 parts of hot water, and dried to obtain 25.2 parts of a compound represented by the following formula (4).

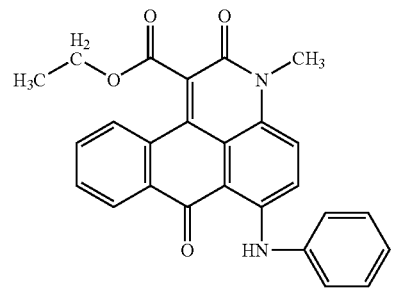

Formula (4)

Example 1

(1) Under water-cooling, 57.8 parts of 31% fuming sulfuric acid was added to 292.2 parts of 96% sulfuric acid at 40° C. or below so as to prepare 12% fuming sulfuric acid.

After 106.0 parts of a compound of the above formula (4) was added to the obtained fuming sulfuric acid at 70° C. or below over 30 minutes, the reaction liquid was raised in temperature to 80 to 90° C. and the reaction was carried out at this temperature for 2 hours. After cooling to 40° C., the reaction liquid was added to 1800 parts of ice water and stirred at room temperature for 30 minutes. After the resulting solution was filtered to remove off insoluble substances, water was added to the filtrate to adjust the volume to 2000 parts, 300 parts of sodium chloride was further added and stirring was carried out for 1.5 hours. The resulting precipitated solid was separated by filtration and washed with 500 parts of a 20% aqueous sodium chloride solution to obtain 210 parts of a dark red cake.

(2) After the cake obtained in Example 1 (1) described above was added to 1000 parts of methanol, heated while stirring, and maintained at 65° C. for 45 minutes, the resulting precipitated solid was separated by filtration and dried to obtain 118 parts of a compound represented by the following formula (5) as red crystals.

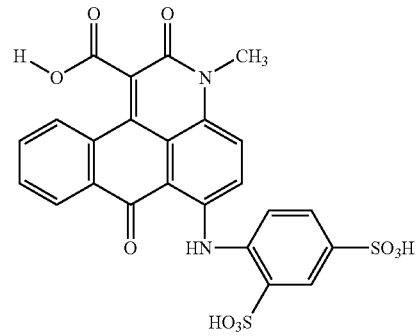

Formula (5)

(3) To 90 parts of water, 18 parts of the compound of the above formula (5) was added and the mixture was stirred, and a 25% aqueous sodium hydroxide solution was added thereto to adjust the pH to 9. After the resulting solution was heated to 75° C., 7.6 parts of benzyl chloride was added dropwise thereto over 1.5 hours and then reaction was carried out at 75 to 80° C. for 3 hours. Subsequently, 3.8 parts of benzyl chloride was added dropwise thereto over 10 minutes and then reaction was carried out for 1 hour, and further 3.8 parts of benzyl chloride was added dropwise thereto over 7 minutes and then reaction was carried out for 4 hours.

After the reaction liquid was filtered to remove off insoluble substances, water was added to the filtrate to adjust the volume to 200 parts. To the filtrate after the adjustment, 30 parts of sodium chloride was added and after stirring for 1 hour, precipitated solid was then separated by filtration. The resulting solid was washed with 150 parts of a 20% aqueous sodium chloride solution to obtain 50 parts of a red cake.

(4) After the cake obtained in Example 1 (3) described above was added to 500 parts of methanol, heated to 60° C. under stirring, and maintained for 30 minutes, the resulting precipitated solid was separated by filtration, washed with 200 parts of methanol, and dried to obtain 17.5 parts of a compound represented by the following formula (2) as red crystals. λmax: 531.2 nm.

Formula (2)

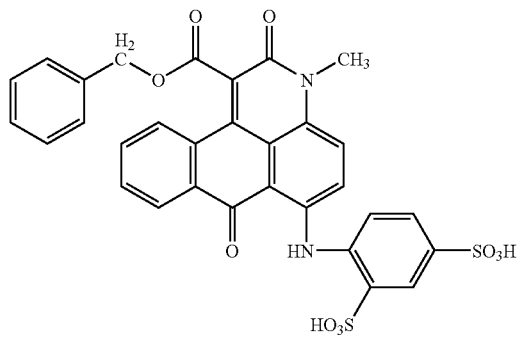

(2)

Example 2

To 45 parts of water, 9.0 parts of the compound of the above formula (5) obtained in Example 1 (2) was added, and a 25% aqueous sodium hydroxide solution was added thereto under stirring to adjust the pH to 5.6 and then heated to 70° C. to obtain a solution. To the obtained solution, 6.6 parts of 1-(chloromethyl)naphthalene was added dropwise over 27 minutes while maintaining at 70 to 75° C. and pH 5.2. Subsequently, the reaction was carried out for 1.5 hours while maintaining the same temperature and pH. After cooling the reaction liquid to 27° C., 60 parts of methanol was added thereto and stirred at room temperature for 2 hours. The resulting precipitated solid was separated by filtration, washed with 100 parts of methanol, and then dried to obtain 5.2 parts of a compound of the following formula (6) as red crystals. λmax: 535.4 nm.

Formula (6)

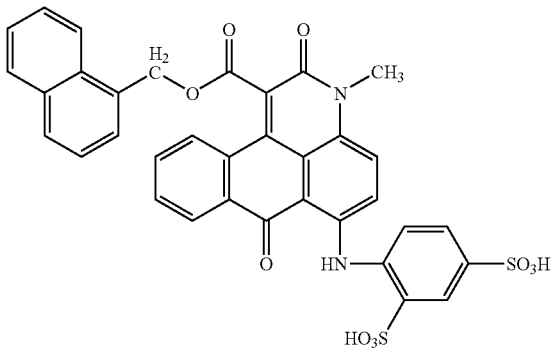

(6)

Examples 3 and 4

(A) Preparation of Ink

Using the compound of the above formula (2) obtained in Example 1 (Compound No. 1 in Table 1), an ink composition having the composition ratio shown in the following Table 2 was prepared and filtered with a 0.45 μm membrane filter to obtain a water-based ink composition for inkjet recording. In this connection, ion-exchanged water was used as water. The ink composition was adjusted by addition of 28% ammonia water and water so that the pH thereof was 8 to 10 and the total amount thereof was 100 parts.

Using the above obtained water-based ink composition for inkjet recording, inkjet recording was performed by the method in (B) described later and evaluation was conducted by the method in (C) described later. This is the end of Example 3.

In addition, using the compound of the above formula (6) obtained in Example 2 (Compound No. 7 in Table 1) instead of the compound of Example 1 in the following Table 2, an ink composition and a water-based ink composition for inkjet recording were likewise prepared. Using the latter, evaluation test was conducted in the same manner as described above. This is Example 4.

TABLE 2

| Compound of Example 1 | 6.0 parts |
|---|---|
| Glycerine | 5.0 parts |
| Urea | 5.0 parts |
| N-Methyl-2-pyrrolidone | 4.0 parts |
| IPA (isopropylalcohol) | 3.0 parts |
| Butyl carbitol | 2.0 parts |
| Surfactant (Surfynol$^{RTM}$ 104PG50; manufactured by Nissin Chemical Industry Co., Ltd.) | 0.1 part |
| 28% Ammonia water + water | 74.9 parts |
| Total | 100.0 parts |

Comparative Example 1 and Comparative Example 2

For comparison, using a compound No. 01 of Example 1-1 in Patent Literature 1 (compound of the following formula (7)) instead of the compound of Example 1 in the above Table 2, an ink composition and a water-based ink composition for inkjet recording were prepared in the same manner as in Example 3, inkjet recording was performed, and evaluation of the recorded image was conducted. This is Comparative Example 1.

In the same manner as in Comparative Example 1 except that a compound No. 36 of Example 7 in Patent Literature 1 (compound of the following formula (8)) was used instead of the compound of Example 1 in Table 2 described above, an ink composition was prepared, inkjet recording was performed, and evaluation of the recorded image was conducted. This evaluation test was Comparative Example 2.

The compound used in Comparative Example 1 and the compound used in Comparative Example 2 are shown in free acid form, but they were synthesized as a sodium salt.

Formula (7)

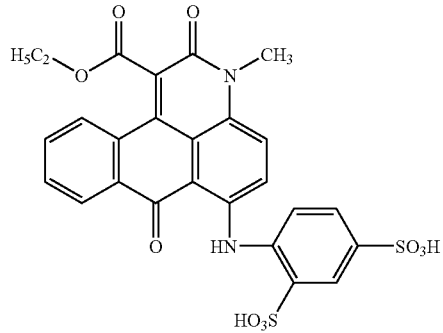

(7)

Formula (8)

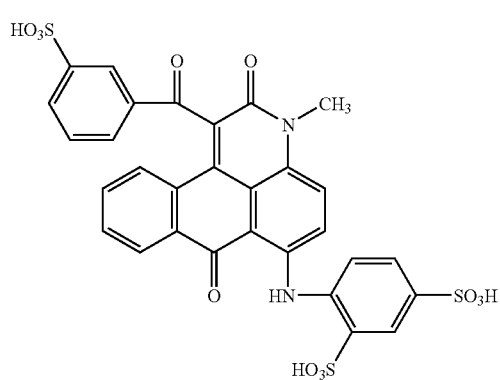

(8)

Example 5

(1) To 540 parts of water, 90 parts of the compound of the formula (5) obtained in Example 1 (2) was added and stirred, and a 25% aqueous sodium hydroxide solution was added thereto to adjust the pH to 8.5 to 9. After the resulting solution was heated to 75 to 80° C., 42.2 parts of m-methylbenzyl chloride was added dropwise thereto over 1 hour while adjusting the pH of the solution to 8.5 to 9 with a 25% aqueous sodium hydroxide solution, and then reaction was carried out at 75 to 80° C. for 3 hours. To the resulting reaction liquid, 21.1 parts of m-methylbenzyl chloride was further added dropwise over 30 minutes, and then reaction was carried out for 3 hours. Further, 21.1 parts of m-methylbenzyl chloride was added dropwise thereto over 30 minutes, and then reaction was carried out for 1 hour. Subsequently, 100 parts of hot water was added thereto and further reaction was carried out for 5 hours. During these dropwise additions and reactions, the pH of the reaction liquid was adjusted to 8.5 to 9 with a 25% aqueous sodium hydroxide solution.

After the reaction liquid was filtered to remove off insoluble substances, water was added to the filtrate to adjust the volume to 2000 parts. Concentrated hydrochloric acid was added to adjust the pH to 1.2, and 240 parts of sodium chloride was added thereto and after stirring for 1 hour, precipitated solid was separated by filtration. The resulting solid was washed with 500 parts of a 20% aqueous sodium chloride solution to obtain 470 parts of a red cake.

(2) To a mixed solvent of 900 parts of methanol and 600 parts of water, 470 parts of the red cake obtained in Example 5 (1) described above was added and stirring was carried out at 60° C. for 2 hours. After that, the resulting precipitated crystals were separated by filtration, washed with 500 parts of methanol, and dried to obtain 109.2 parts of a compound represented by the following formula (9) as red crystals. λmax: 529 nm.

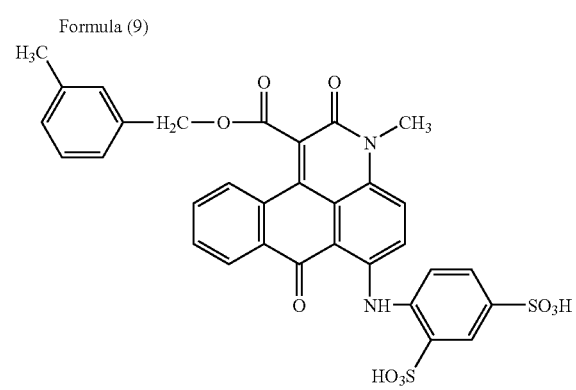

(9)

Example 6

(A) Preparation of Ink

By the same method as in Example 3 except that the compound of the above formula (9) obtained in Example 5 (Compound No. 3 in Table 1) was used instead of the compound of Example 1 in Table 2 described above, an ink composition and a water-based ink composition for inkjet recording were prepared. Using the latter of these, evaluation test was conducted in the same manner as in Example 3.

(B) Inkjet Printing

Using an inkjet printer (Pixus® iP4100, manufactured by Canon Inc.), inkjet recording was performed on the following 3 types of glossy papers 1 to 3 (record-receiving material) having an ink image receiving layer containing a porous white inorganic substance. An image pattern was made so that several gradations of print density can be obtained in inkjet recording, and printing matters were prepared.

Glossy papers used are as follows:

Glossy paper 1: Professional Photopaper PR-101 (trade name), manufactured by Canon Inc.;

Glossy paper 2: CRISPIA® (trade name) manufactured by Seiko Epson Corporation;

Glossy paper 3: Advanced Photo Paper (trade name) manufactured by Hewlett-Packard Development Company (HP).

(C) Evaluation of Recorded Image

Hue Evaluation on Glossy Paper

As for hue and vividness of recorded image, using a calorimetric system (GRETAG® SPM50; manufactured by GretagMacbeth AG), recording papers printed (which have the same print density (D value), respectively) were measured, L*, a* and b* values were calculated, and color saturation (C*) showing vividness was calculated from $C^* = ((a^*)^2 + (b^*)^2)^{1/2}$ using chromaticity (a*, b*). Hue evaluation was conducted in comparison with a sample of Standard Magenta in Japan Color (JNC) of JPMA (which is an incorporated company: Japan Printing Machinery Manufacturers Association).

The results of the hue evaluation for Examples 3, 4 and 6 are shown in Table 3. In this connection, the paper used for Standard Magenta in Japan Color is Japan Color Standard Paper.

TABLE 3

| | Brightness | Chromaticity | | Color saturation |
|---|---|---|---|---|
| | L* | a* | b* | C* |
| JNC Standard Magenta | 46.3 | 74.4 | −4.8 | 74.6 |
| Glossy paper 1 | | | | |
| Example 3 | 42.3 | 83.1 | −16.7 | 84.8 |
| Example 4 | 42.7 | 82.6 | −13.0 | 83.6 |
| Example 6 | 42.9 | 84.7 | −21.8 | 87.5 |
| Comparative Example 1 | 45.7 | 84.0 | −15.1 | 85.1 |
| Comparative Example 2 | 43.5 | 83.6 | −25.0 | 84.8 |
| Glossy paper 2 | | | | |
| Example 3 | 42.3 | 85.7 | −21.3 | 88.5 |
| Example 4 | 44.5 | 86.0 | −16.2 | 87.6 |
| Example 6 | 44.6 | 87.0 | −20.5 | 89.4 |
| Comparative Example 1 | 45.3 | 86.4 | −21.2 | 89.1 |
| Comparative Example 2 | 42.5 | 86.8 | −33.5 | 88.5 |
| Glossy paper 3 | | | | |
| Example 3 | 42.1 | 84.6 | −21.5 | 87.4 |
| Example 4 | 44.8 | 86.0 | −17.3 | 87.7 |
| Example 6 | 43.9 | 84.9 | −21.0 | 87.4 |
| Comparative Example 1 | 44.4 | 85.4 | −19.0 | 87.8 |
| Comparative Example 2 | 43.1 | 85.3 | −30.5 | 87.3 |

As is clear from Table 3, it is found that in any of the glossy papers, the hues (a*, b*) of Examples 3, 4, 6 and Comparative Example 1 are closer to the hue of JNC Standard Magenta compared with that of Comparative Example 2.

In particular, Comparative Example 2 has b* value of −25.0 on glossy paper 1 (Examples 3, 4 and 6 have a value of −13.0 to −16.7), −33.5 on glossy paper 2 (Examples 3, 4 and 6 have a value of −16.2 to −21.3), and −30.5 on glossy paper 3 (Examples 3, 4 and 6 have a value of −17.3 to −21.5), and thus has a considerably low value compared with b* values of Examples 3, 4 and 6, whereby it is found that the hue of Comparative Example 2 has a blue tinge. In the view of approximation to the hue of JNC Standard Magenta, it can be said that the hue of each Example of the present invention is more approximate than the hue of Comparative Example 2.

Judging from the results mentioned above, the recorded image of the ink composition using the compound of the present invention has a hue closer to JNC Standard Magenta than the hue of Comparative Example 2. Therefore, it can be said that the anthrapyridone compound of the present invention is suitable as a magenta coloring matter for inkjet recording.

Hereinafter, evaluation of various fastnesses will be described. As for fastnesses, 3 types of tests, "(D) light fastness test of recorded image", "(E) ozone gas fastness test of recorded image" and "(F) moisture fastness test of recorded image" were conducted for evaluation.

(D) Light Fastness Test of Recorded Image

Using a low temperature xenon weatherometer XL 75 (manufactured by Suga Test Instruments Co., Ltd.), test pieces printed respectively on glossy papers 1 to 3 were irradiated at an illuminance of 10K lux for 96 hours under the circumstances of a temperature of 24° C. and a humidity of 60% RH. Using a colorimetric system (GRETAG® SPM50; manufactured by GretagMacbeth AG), color difference (ΔE) of print density (D value=in the vicinity of 1.2) was measured before and after the irradiation and evaluated in 4 levels. The results are shown in Table 4.

5>ΔE . . . ⊚
10>ΔE≧5 . . . ○
16>ΔE≧10 . . . Δ
ΔE≧16 . . . X

(E) Ozone Gas Fastness Test of Recorded Image

Using an ozone weatherometer (manufactured by Suga Test Instruments Co., Ltd.), test pieces printed respectively on glossy papers 1 to 3 were left for 8 hours at an ozone concentration of 10 ppm, a temperature of 24° C. and a humidity of 60% RH. Color difference (ΔE) of print density (D value=in the vicinity of 1.2) was measured before and after the irradiation and evaluated in 4 levels. The results are shown in Table 4.

5≧ΔE . . . ⊚
10≧ΔE>5 . . . ○
15≧ΔE>10 . . . Δ
ΔE>15 . . . X

(F) Moisture Fastness Test of Recorded Image

Using a thermo-hygrostat (manufactured by Ohken Co., Ltd), test pieces printed respectively on glossy papers 1 to 3 were left for 96 hours at a temperature of 30° C. and a humidity of 80% RH. Bleeding property was judged by visual observation before and after the test and evaluated in 3 levels. The results are shown in Table 4.

○: bleeding is not observed
Δ: bleeding is slightly observed
X: bleeding is significantly observed

TABLE 4

| | Light fastness | Ozone gas fastness | Moisture fastness |
|---|---|---|---|
| Glossy paper 1 | | | |
| Example 3 | ○ | ○ | ○ |
| Example 4 | ○ | ○ | ○ |
| Example 6 | ○ | ○ | ○ |
| Comparative Example 1 | ○ | ○ | Δ |
| Comparative Example 2 | X | ○ | Δ |
| Glossy paper 2 | | | |
| Example 3 | ○ | ⊚ | Δ |
| Example 4 | ○ | ⊚ | ○ |
| Example 6 | ○ | ⊚ | ○ |
| Comparative Example 1 | ○ | ⊚ | X |
| Comparative Example 2 | X | ○ | X |
| Glossy paper 3 | | | |
| Example 3 | ⊚ | ⊚ | Δ |
| Example 4 | ⊚ | ⊚ | ○ |
| Example 6 | ⊚ | ⊚ | ○ |
| Comparative Example 1 | ⊚ | ⊚ | X |
| Comparative Example 2 | ○ | ⊚ | X |

From Table 4, the following judgment is made.

With regard to light fastness, Comparative Example 2 is marked by X (ΔE≧16) for glossy papers 1 and 2, and by ○ (10>ΔE≧5) for glossy paper 3. Examples 3, 4 and 6 and Comparative Example 1 are marked by ○ (10>ΔE≧5) for glossy papers 1 and 2, and by ⊚ (5>ΔE) for glossy paper 3, and compared with these, Comparative Example 2 has a larger color difference before and after the test. Therefore, it is found that Examples 3, 4 and 6 have a more excellent light fastness than Comparative Example 2.

With regard to moisture fastness, Comparative Examples caused a slightly observed bleeding in glossy paper 1 and thus has a relatively good moisture fastness, but they caused a significantly observed bleeding in glossy papers 2 and 3. On the other hand, Examples 3, 4 and 6 caused no bleeding in any of the glossy papers, except that Example 3 caused a slightly observed bleeding in glossy papers 2 and 3. Therefore, it is found that Examples 3, 4 and 6 have a more excellent moisture fastness than Comparative Examples.

With regard to ozone gas fastness, Examples and Comparative Examples are all marked by ○ (10≧ΔE>5) for glossy paper 1 and by ⊚ (5≧ΔE) for glossy paper 3, showing that they have good results in the same range. However, Examples and Comparative Example 1 are marked by ⊚ (5≧ΔE) for glossy paper 2, and by comparison, only Comparative Example 2 is marked by ○ (10≧ΔE>5) and thus has a larger color difference before and after the test compared with the other examples. Therefore, it is found that Examples 3, 4 and 6 have a more excellent ozone fastness than Comparative Example 2.

From the above results, it is clear that the anthrapyridone compound of the present invention is a coloring matter which provides images excellent in various fastnesses, i.e. not only ozone fastness and light fastness but also moisture fastness in particular. Also in this regard, the anthrapyridone compound of the present invention is extremely useful as a magenta coloring matter for inkjet recording.

The invention claimed is:

1. An anthrapyridone compound represented by the following formula (1) or a salt thereof:

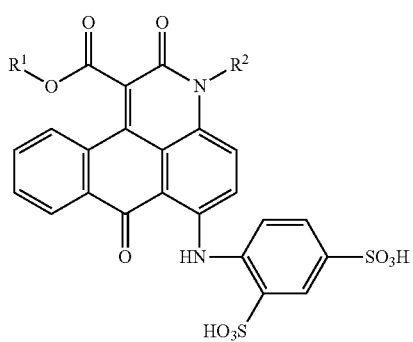

(1)

wherein R¹ represents a benzyl group wherein the phenyl group in the benzyl group may be substituted by a group selected from the group consisting of a methyl group, a chlorine atom and a nitro group; a 1-naphthylmethyl group, a phenacyl group or a cyanopropyl group, and R² represents a hydrogen atom, an alkyl group, a lower alkoxy lower alkyl group, a hydroxy lower alkyl group, a cyclohexyl group, a mono- or dialkylamino alkyl group or a cyano lower alkyl group, respectively.

2. The anthrapyridone compound or a salt thereof according to claim 1, wherein R¹ is a benzyl group wherein the phenyl group in the benzyl group may be substituted by a group selected from the group consisting of a methyl group, a chlorine atom and a nitro group; a 1-naphthylmethyl group, a phenacyl group or a 3-cyanopropyl group, and R² is a hydrogen atom, a C1 to C4 alkyl group, a C1 to C4 alkoxy C1 to C4 alkyl group, a hydroxy C1 to C4 alkyl group, a cyclohexyl group, a (mono or di-C1 to C4 alkylamino) C1 to C4 alkyl group or a cyano C1 to C4 alkyl group.

3. The anthrapyridone compound or a salt thereof according to claim 1, wherein R¹ is a benzyl group wherein the phenyl group in the benzyl group may be substituted by a group selected from the group consisting of a methyl group, a chlorine atom and a nitro group; a 1-naphthylmethyl group, a phenacyl group or a 3-cyanopropyl group, and R² is a hydrogen atom, a C1 to C4 alkyl group, a 3-methoxypropyl group, a 2-hydroxyethyl group, a 3-dimethylaminopropyl group or a 2-cyano ethyl group.

4. The anthrapyridone compound or a salt thereof according to claim 1, wherein R¹ is a benzyl group wherein the phenyl group in the benzyl group may be substituted by a group selected from the group consisting of a methyl group, a chlorine atom and a nitro group; and R² is a C1 to C4 alkyl group.

5. The anthrapyridone compound or a salt thereof according to claim 1, wherein R¹ is benzyl, methylbenzyl or 1-naphthylmethyl, and R² is methyl.

6. The anthrapyridone compound or a salt thereof according to claim 1, which is represented by the following formula (2):

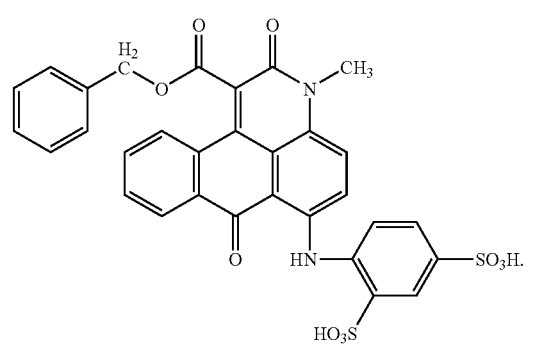

(2)

7. The anthrapyridone compound or a salt thereof according to claim 1, which is represented by the following formula (9):

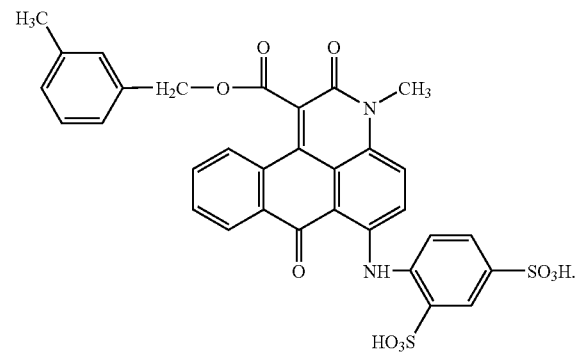

(9)

8. An ink composition comprising the anthrapyridone compound or a salt thereof according to claim 1.

9. The ink composition according to claim 8, which contains water and a water-soluble organic solvent.

10. The ink composition according to claim 9, which is for inkjet recording.

11. The ink composition according to claim 8, wherein the content of an inorganic salt contained in the total amount of the anthrapyridone compound or a salt thereof according to claim 1 is 1% by weight or below.

12. The ink composition according to any one of claims 8 to 11, wherein the content of the anthrapyridone compound represented by the following formula (1) or a salt thereof:

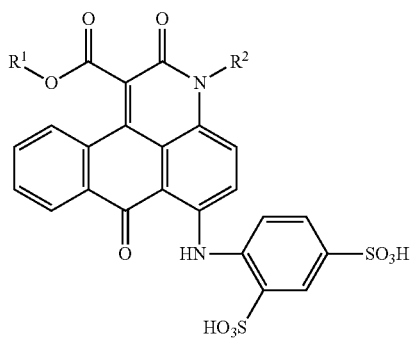

(1)

wherein $R^1$ represents a benzyl group wherein the phenyl group in the benzyl group may be substituted by a group selected from the group consisting of a methyl group, a chlorine atom and a nitro group; a 1-naphthylmethyl group, a phenacyl group or a cyanopropyl group, and $R^2$ represents a hydrogen atom, an alkyl group, a lower alkoxy lower alkyl group, a hydroxy lower alkyl group, a cyclohexyl group, a mono- or di-alkylamino alkyl group or a cyano lower alkyl group, respectively, is 0.1 to 20% by weight.

13. An inkjet recording method comprising discharging droplets of the ink composition according to claim 8 in response to a recording signal to record on a record-receiving material.

14. The inkjet recording method according to claim 13, wherein the record-receiving material is a communication sheet.

15. The inkjet recording method according to claim 14, wherein the communication sheet has an ink receiving layer containing a porous white inorganic substance.

16. A colored product colored with the ink composition according to claim 8.

17. The colored product according to claim 16, wherein coloring is carried out by an inkjet printer.

18. An inkjet printer in which a container containing the ink composition according to claim 8 is installed.

* * * * *